July 3, 1951 H. A. VERSCHUREN Plant Pat. 1,019
ROSE PLANT
Filed March 31, 1950
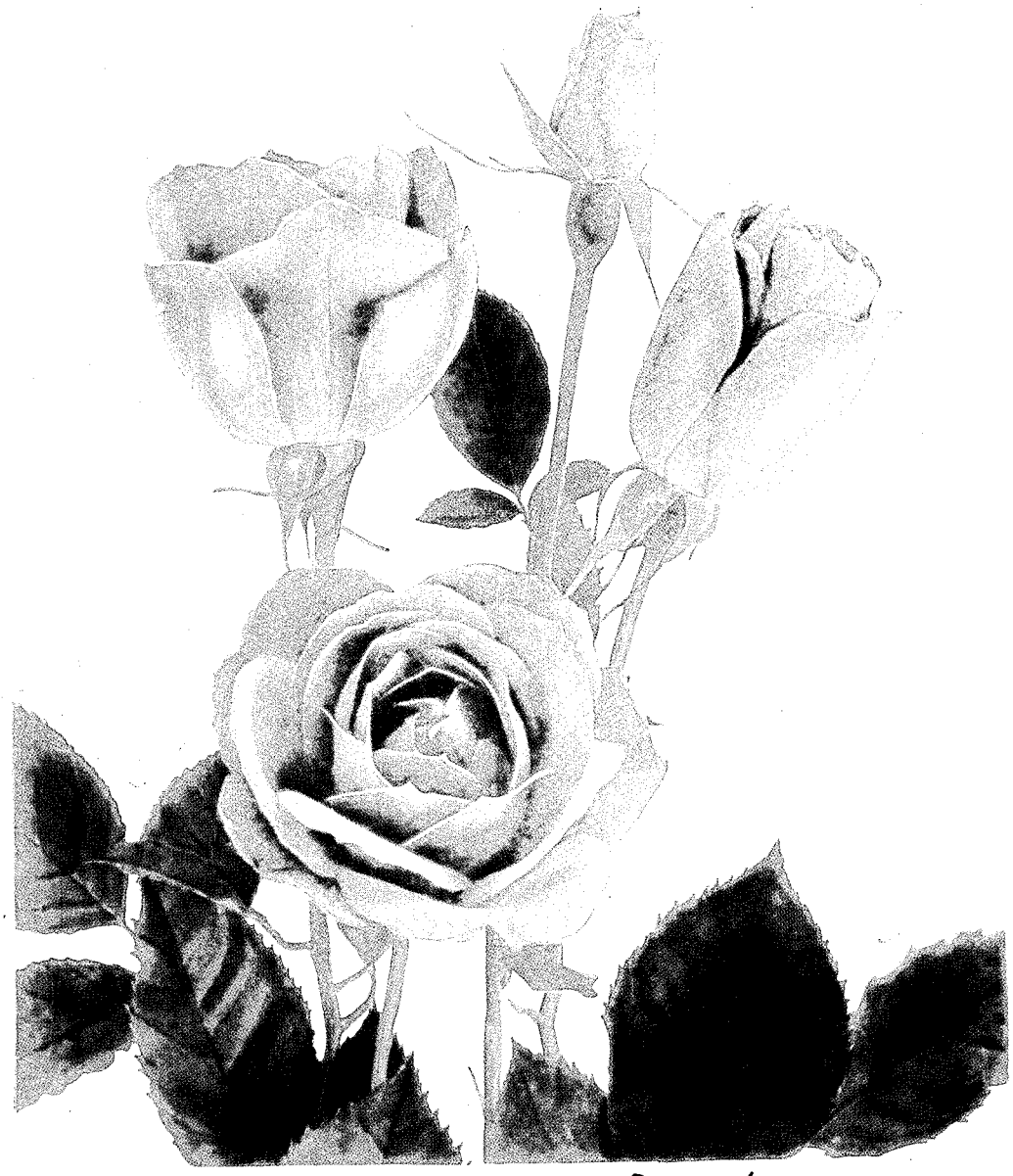
Inventor.
Hens A. Verschuren, Deceased
By: Maria Theresia Antonetta Verschuren
Legal Representative
By: Robb & Robb
Attorneys Patented July 3, 1951

Plant Pat. 1,019

UNITED STATES PATENT OFFICE 1,019

ROSE PLANT

Hens A. Verschuren, deceased, late of Haps, Netherlands, by Maria Theresia Antonetta Verschuren, legal representative, Haps, Netherlands, assignor, by mesne assignments, to Charles H. Totty Company, Madison, N. J., a corporation of New Jersey Application March 31, 1950, Serial No. 153,216

1 Claim. (Cl. 47—61)

The present invention relates to a new and distinct variety of hybrid tea rose plant, originated by crossing a selected seedling of "Ulrich Brunner" × "Westfield Star," (which are two varieties about which little is known, as they have never been introduced commercially in this country), and a selected seedling of the two well-known varieties "Chieftain" (Plant Patent No. 150) × "Better Times" (Plant Patent No. 23).

This new variety is completely distinct from any rose known in commerce, including its parent varieties, and differs primarily from other red roses by the exceptionally brilliant scarlet color, most nearly resembling currant red, and velvety texture of the flowers.

Among other distinguishing characteristics are: the flowers of this new variety hold their color without fading or "bluing" until the petals drop; the buds are exceptionally long and very flat or square (that is, blunt at the tip) because the petals are all of the same length; the petals are very round and have two notches which form one sharp point in each petal, showing even in the tight bud, and in the open flower when the petals open back flat, make the flower star-like in appearance; the foliage is of a very light shade of green for a red rose, and the edges of the foliage are deeply serrated; and the variety is a more prolific bloomer than any other greenhouse rose known to date and is very free from mildew and black spot.

This new variety most nearly resembles the variety "Chieftain" in the shape of the bud, but the color of the flowers is much more scarlet than "Chieftain" and the color holds better and does not "blue" as "Chieftain" does. While the young growth of "Chieftain" is reddish-green, the young growth of the new variety is a lighter bronze-green. The new variety is more productive and more resistant to disease than "Chieftain."

As compared with the variety "Better Times," the new variety has a long square bud instead of a long pointed bud like "Better Times." The flowers of the new variety have fewer petals than the flowers of "Better Times," but the color of the flowers of the new variety is a more brilliant scarlet and holds better than the cerise color of "Better Times" which tends to blue when fading. The foilage of "Better Times" is a leathery dark green, while the foliage of the new variety is a soft light green and is deeply serrated. The new growth of "Better Times" is red in color, while that of the new variety is bronze-green.

Taking all of the distinctive features of this new variety into consideration, it may be stated that from a commercial standpoint, it has all the characteristics of a rose that are desirable and necessary for a good greenhouse rose.

Asexual reproduction of this new variety by budding at Haps, Holland, and by grafting at Madison, New Jersey, U. S. A., shows that the foregoing characteristics come true to form and are established and transmitted through suceeding propagations.

In the drawing are illustrated specimens of the new rose variety, with the flowers in various stages of development from small bud to full-open flower.

The following is a detailed description of the new variety, color terminology being in accord with ordinary dictionary definiton except where otherwise indicated by reference to Wilson's Colour Chart or to Ridgway's Color Standards and Nomenclature.

Observations were made at Madison, New Jersey.

Type: Hardy; greenhouse; for cut flowers.
Class: Hybrid tea.
Breeding or discovery: Seedling.
*Seed parent.*—Seedling of "Ulrich Brunner" × "Western Star."
*Pollen parent.*—Seedling of "Chieftain" × "Better Times."

*Flower*

Continuity: Continuous.
Fragrance: Slight.
Flowers borne: Singly to stem; on strong, medium length stems.
Quantity of bloom: Abundant in greenhouse.
Bud:
*Peduncle.*—Long; medium heavy; erect; light green; almost smooth; few yellow hairs.
*Before calyx breaks.*—Size—medium. Form—pointed; with slender foliaceous parts extending beyond the tip of the bud equal to one-fourth of its length. Color—Uranium Green (#63 Wilson's Colour Chart) suffused with Jasper Red (#018 Wilson's Colour Chart).
*As calyx breaks.*—Color—Ruby Red (#827, Wilson's Colour Chart).
*As first petal opens.*—Size—medium. Form—Long and ovoid; blunt tip. Color—Deep Currant Red (#821 Wilson's Colour Chart) with Indian Yellow (#6/1 Wilson's Colour Chart) base.
*Opening.*—Opens up well.

Bloom: Size, when fully open—large; 4" to 6".

*Petalage.*—Double; from 25 to 32 petals arranged regularly.

*Form.*—Globular; petals remaining at first loosely rolled outward; becoming later, at maturity, flat cupped.

Petals: Leathery with inside and outside velvety.

*Shape.*—Outside—round with two notches. Intermediate—round with two notches. Inside—oval.

*Color.*—Colors may be modified by being penciled.

This description of a newly opened flower was made from a rose grown in a greenhouse in the month of January, 1950, at Madison, New Jersey:

*Color.*—*Outside petal*—outside surface: Currant Red (#821 Wilson's Colour Chart); inside surface: Brilliant velvety Currant Red (#821 Wilson's Colour Chart) with Indian Yellow (page 6, shade 6/1 Wilson's Colour Chart) base; *Intermediate petal*—outside surface: Currant Red (#821 Wilson's Colour Chart); inside surface: Brilliant velvety Currant Red (#821 Wilson's Colour Chart) with Indian Yellow (page 6, shade 6/1 Wilson's Colour Chart), base. *Inner petal*—outside surface: Currant Red (#821 Wilson's Colour Chart); inside surface: Brilliant velvety Currant Red (#821 Wilson's Colour Chart) with Indian Yellow (page 6, shade 6/1 Wilson's Colour Chart), base.

This description was made from a rose that was open for three days in a greenhouse in the month of December, 1949, at Madison, New Jersey:

*Color.*—*Outside petal*—outside surface: Currant Red (#821 Wilson's Colour Chart). Inside surface: Velvety Currant Red (#821 Wilson's Colour Chart) with Indian Yellow (page 6, shade 6/1 Wilson's Colour Chart) base. *Inside petal*—outside surface: Currant Red (#821 Wilson's Colour Chart); inside surface: Velvety Currant Red (#821 Wilson's Colour Chart) with Indian Yellow (page 6, shade 6/1 Wilson's Colour Chart) base.

*General color effect.*—Newly opened flower—brilliant scarlet. Three days open—brilliant scarlet.

*Behavior.*—Drop off cleanly; color unaffected by intense heat.

*Flower longevity.*—Cut roses grown in greenhouse kept at living room temperatures—5 or 6 days in December.

*Reproductive organs*

Stamens: Many; arranged regularly about pistils.

Filaments: Medium length; reddish; most with anthers.

Anthers: Large; orange to yellow; open at various times.

Pollen: Moderately abundant; gold.

Pistils: Medium number.

Styles: Uneven; medium length; separated.

Stigma: Yellow.

Ovaries: All enclosed in calyx.

Hips: Long; ovoid; green gray; moderately smooth; thin.

*Plant*

Foliage:

*Leaves.*—Compound of five leaflets; normally abundant.

*Leaflets.*—Shape—oval with apex obtuse; base round; margin serrate.

*Color.*—*Mature*—The mature leaf is dusky yellowish green (#41 Ridgway's) but the foliage is shiny and glossy. *Young*—On the new or immature growth the inside of the leaves are dark, dull, yellow green (#32 Ridgway's) edged with Vinaceous Brown (#39 Ridgway's). The reverse side is Pois Green (#41 Ridgway's), washed with Vinaceous Brown (#39 Ridgway's).

*Rachis.*—Medium heavy. Upper side: grooved; hairy; under side: moderately smooth.

*Stipules.*—Long; narrow; with long points turning out at an angle of more than 45°.

*Disease.*—Resistant to mildew and black spot.

Growth:

*Habit.*—Upright; little branched.

*Growth.*—Moderately vigorous.

*Canes.*—Medium heavy.

*Main stems.*—Dull green. *Thorns*—several; medium length; hooked downward; with narrow base. *Prickles*—few; bronze. *Hairs*—none.

*Branches.*—Dull green. *Thorns*—several; medium length; hooked downward; with narrow base. *Color*—Grape Green (#41 Ridgway's). *Prickles*—few; brown. *Hairs*—none.

*New shoots.*—Dull bronze. *Thorns*—several; medium length; hooked downward; with narrow base. *Color*—Grape Green (#41 Ridgway's) washed with Vinaceous Brown (#39 Ridgway's). *Prickles and hairs*—none.

What is claimed is:

A new and distinct variety of rose plant of the hybrid tea class, characterized as to novelty by the non-fading and non-bluing brilliant scarlet color and velvety texture of its flowers, by the long blunt-tip shape of the buds, by the round and double-notched form of the petals, defining a point in each petal and showing even in the tight bud, while giving the open flower a star-like appearance, by the light green color and deeply serrated edges of its foliage, by its prolific blooming habit, and by its resistance to mildew and black spot, substantially as shown and described.

MARIA THERESIA
ANTONETTA VERSCHUREN,
*Legal Representative of the Estate of Hens A. Verschuren, Deceased.*

No references cited.